US012251098B2

United States Patent
Bagley et al.

(10) Patent No.: US 12,251,098 B2
(45) Date of Patent: Mar. 18, 2025

(54) SUTURE BASED CLOSURE DEVICE

(71) Applicant: BOSTON SCIENTIFIC SCIMED, INC., Maple Grove, MN (US)

(72) Inventors: Kevin L. Bagley, Natick, MA (US); Christopher R. Deuel, Melrose, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 389 days.

(21) Appl. No.: 17/729,816

(22) Filed: Apr. 26, 2022

(65) Prior Publication Data

US 2022/0338866 A1    Oct. 27, 2022

Related U.S. Application Data

(60) Provisional application No. 63/179,966, filed on Apr. 26, 2021.

(51) Int. Cl.
| | | |
|---|---|---|
| *A61B 17/04* | (2006.01) | |
| *A61B 17/062* | (2006.01) | |
| *A61B 17/06* | (2006.01) | |

(52) U.S. Cl.
CPC ...... *A61B 17/0485* (2013.01); *A61B 17/0469* (2013.01); *A61B 17/0482* (2013.01);
(Continued)

(58) Field of Classification Search
CPC ............ A61B 17/0469; A61B 17/0625; A61B 2017/00296; A61B 17/0482; A61B 2017/06047; A61B 2017/0609; A61B 17/062; A61B 17/06061; A61B 1/018; A61B 17/00234; A61B 17/04; A61B 17/0491; A61B 17/29; A61B 2017/0034; A61B 2017/00349; A61B 2017/047
See application file for complete search history.

(56) References Cited

U.S. PATENT DOCUMENTS

| | | |
|---|---|---|
| 5,478,344 A | 12/1995 | Stone |
| 5,584,861 A | 12/1996 | Swain et al. |

(Continued)

FOREIGN PATENT DOCUMENTS

| | | |
|---|---|---|
| CA | 2682488 A1 | 10/2008 |
| DE | 202005022017 U1 | 5/2012 |

(Continued)

OTHER PUBLICATIONS

International Search Report and Written Opinion dated Aug. 20, 2019 for International Application No. PCT/US2019/033748.
(Continued)

*Primary Examiner* — Katherine M Shi
(74) *Attorney, Agent, or Firm* — Seager, Tufte & Wickhem, LLP

(57) ABSTRACT

A medical device includes a suture ring that defines an arcuate channel extending therein. A first arcuate needle passer is slidingly disposed within a first side of the arcuate channel and a second arcuate needle passer is slidingly disposed within a second side of the arcuate channel. A suture shuttle is passable between the first arcuate needle passer and the second arcuate needle passer and is configured to be releasably securable to the first arcuate needle passer and to the second arcuate needle passer.

20 Claims, 7 Drawing Sheets

(52) U.S. Cl.
CPC .. *A61B 17/0625* (2013.01); *A61B 2017/0472* (2013.01); *A61B 2017/06009* (2013.01); *A61B 2017/06042* (2013.01)

(56) References Cited

U.S. PATENT DOCUMENTS

| | | | |
|---|---|---|---|
| 6,086,608 A | 7/2000 | Ek et al. |
| 6,200,329 B1 | 3/2001 | Fung et al. |
| 6,494,888 B1 | 12/2002 | Laufer et al. |
| 6,506,196 B1 | 1/2003 | Laufer |
| 6,554,845 B1 | 4/2003 | Fleenor et al. |
| 6,569,085 B2 | 5/2003 | Kortenbach et al. |
| 6,626,917 B1 | 9/2003 | Craig |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 8,057,494 B2 | 11/2011 | Aufer et al. |
| 8,062,314 B2 | 11/2011 | Sixto, Jr. et al. |
| 8,066,721 B2 | 11/2011 | Kortenbach et al. |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale |
| 8,425,555 B2 | 4/2013 | Page et al. |
| 8,454,631 B2 | 6/2013 | Viola et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,585,720 B2 | 11/2013 | Gross et al. |
| 8,632,553 B2 | 1/2014 | Sakamoto et al. |
| 8,641,728 B2 | 2/2014 | Stokes et al. |
| 8,679,136 B2 | 3/2014 | Mitelberg |
| 8,709,022 B2 | 4/2014 | Stone et al. |
| 8,764,771 B2 | 7/2014 | Chu |
| 8,882,785 B2 | 11/2014 | DiCesare et al. |
| 8,926,634 B2 | 1/2015 | Rothe et al. |
| 8,992,570 B2 | 3/2015 | Gambale et al. |
| 9,011,466 B2 | 4/2015 | Adams et al. |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,320,515 B2 | 4/2016 | Dana et al. |
| 9,486,126 B2 | 11/2016 | West et al. |
| 9,504,465 B2 | 11/2016 | Chu |
| 9,510,817 B2 | 11/2016 | Saadat et al. |
| 9,549,728 B2 | 1/2017 | Chu |
| 9,750,494 B2 | 9/2017 | Gross et al. |
| 9,788,831 B2 | 10/2017 | Mitelberg |
| 9,844,366 B2 | 12/2017 | Woodard, Jr. et al. |
| 9,867,610 B2 | 1/2018 | Mitelberg et al. |
| 10,045,871 B2 | 8/2018 | Saadat et al. |
| 10,143,463 B2 | 12/2018 | Dana et al. |
| 10,194,902 B2 | 2/2019 | Nobles et al. |
| 10,335,142 B2 | 7/2019 | Raybin et al. |
| 2002/0107530 A1 | 8/2002 | Sauer et al. |
| 2003/0195529 A1 | 10/2003 | Takamoto et al. |
| 2003/0204205 A1 | 10/2003 | Sauer et al. |
| 2004/0002699 A1 | 1/2004 | Ryan et al. |
| 2004/138706 A1 | 7/2004 | Abrams et al. |
| 2005/0033319 A1 | 2/2005 | Gambale et al. |
| 2005/0250985 A1 | 11/2005 | Saadat et al. |
| 2006/0282094 A1 | 12/2006 | Stokes et al. |
| 2007/0270908 A1 | 11/2007 | Stokes et al. |
| 2008/0086148 A1 | 4/2008 | Baker et al. |
| 2009/0177031 A1 | 7/2009 | Surti et al. |
| 2010/0137681 A1 | 6/2010 | Ewers et al. |
| 2010/0198006 A1 | 8/2010 | Greenburg et al. |
| 2011/0152891 A1 | 6/2011 | McLawhorn et al. |
| 2011/0276064 A1 | 11/2011 | Henrichsen et al. |
| 2012/0158023 A1 | 6/2012 | Miltelberg et al. |
| 2012/0271327 A1 | 10/2012 | West et al. |
| 2012/0277768 A1 | 11/2012 | Viola et al. |
| 2013/0096581 A1 | 4/2013 | Gilkey et al. |
| 2013/0304093 A1 | 11/2013 | Serina et al. |
| 2014/0121457 A1 | 5/2014 | Mort et al. |
| 2014/0128668 A1 | 5/2014 | Cox et al. |
| 2015/0126983 A1 | 5/2015 | Alvarado et al. |
| 2016/0045197 A1 | 2/2016 | Mitelberg et al. |
| 2017/0035413 A1 | 2/2017 | Takahashi |
| 2017/0042534 A1 | 2/2017 | Nobles et al. |
| 2017/0086817 A1 | 3/2017 | Mitelberg |
| 2017/0086818 A1 | 3/2017 | Mitelberg |
| 2017/0119371 A1 | 5/2017 | Mims et al. |
| 2017/0319197 A1 | 11/2017 | Gross et al. |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |
| 2018/0221009 A1 | 8/2018 | Mitelberg et al. |
| 2018/0235604 A1 | 8/2018 | Comee et al. |
| 2018/0344501 A1 | 12/2018 | Saadat et al. |
| 2019/0374218 A1* | 12/2019 | Ostrovsky .......... A61B 1/00087 |

FOREIGN PATENT DOCUMENTS

| | | | |
|---|---|---|---|
| EP | 1354558 A2 | 10/2003 |
| EP | 1520509 A1 | 4/2005 |
| EP | 2108304 A2 | 10/2009 |
| EP | 2515767 A1 | 7/2011 |
| JP | 2003305046 A | 10/2003 |
| NO | 2018156603 A1 | 8/2018 |
| WO | 0101868 A1 | 1/2001 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |

(56) References Cited

FOREIGN PATENT DOCUMENTS

| WO | 2010085793 | A1 | 7/2010 |
| WO | 2012096280 | A1 | 7/2012 |
| WO | 2013022959 | A2 | 2/2013 |
| WO | 2016200811 | A1 | 12/2016 |
| WO | 2017087856 | A1 | 5/2017 |
| WO | 2021202508 | A1 | 10/2021 |

OTHER PUBLICATIONS

International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
International Search Report and Written Opinion dated Nov. 18, 2019 for International Application No. PCT/US2019/049774.
International Search Report and Written Opinion dated Sep. 20, 2019 for International Application No. PCT/US2019/039312.
International Search Report and Written Opinion dated Jun. 17, 2021 for International Application No. PCT/US2021/024855.
Korean Intellectual Property Office, Office Action, KR Application No. 10-2019-7027516, Mar. 29, 2021 (11 pgs).
International Search Report and Written Opinion dated May 22, 2018 for International Application No. PCT/US2018/018982.
International Search Report and Written Opinion dated Aug. 4, 2022 for International Application No. PCT/US2022/026369.

* cited by examiner

SUTURE BASED CLOSURE DEVICE

CROSS REFERENCE TO RELATED APPLICATIONS

This application claims the benefit of and priority to U.S. Provisional Patent Application Ser. No. 63/179,966 filed on Apr. 26, 2021, the disclosure of which is incorporated herein by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for hemostasis clips to easily bridge and thus help to close the defect. Examples of such endoscopic treatments include removal of large lesions, tunneling under the mucosal layer, full thickness removal of tissue, treating other organs by passing outside of the gastrointestinal tract, and repair of post-surgical issues such as post-surgical leaks, failing surgical staple lines and anastomotic leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. In an example, a suture device includes a mounting structure that is connectable to a distal end of an endoscope. A suture ring is secured to the mounting structure and defines an arcuate channel extending within the suture ring from a first open end to a second open end, the suture ring including a first region proximate the first open end and a second region proximate the second open end. A first arcuate needle passer is slidingly disposed within a first side of the arcuate channel, the first arcuate needle pass including a first arcuate tissue puncturing member and a first control end. A second arcuate needle passer is slidingly disposed within a second side of the arcuate channel, the second arcuate needle passer including a second arcuate tissue puncturing member and a second control end. A suture shuttle is reversibly securable to each of the first arcuate needle passer and the second arcuate needle passer such that the suture shuttle can be passed therebetween.

Alternatively or additionally, the suture shuttle may include a shuttle body defining a straight lumen extending therethrough, the shuttle body configured to fit at least partially within the first region and/or the second region.

Alternatively or additionally, the suture shuttle may be releasably securable to the first arcuate needle passer via an interference fit between the first arcuate tissue puncturing member and the straight lumen.

Alternatively or additionally, the suture shuttle may be releasably securable to the second arcuate needle passer via an interference fit between the second arcuate tissue puncturing member and the straight lumen.

Alternatively or additionally, the suture device may further include a first control element operably coupled to the first control end such that translation of the first control element causes the first arcuate needle passer to move within the arcuate channel and a second control element operably coupled to the second control end such that translation of the second control element causes the second arcuate needle passer to move within the arcuate channel.

Alternatively or additionally, the suture ring may extend in a circle from the first open end to the second open end, the first open end and the second open end spaced apart a distance that permits tissue to extend therebetween.

Alternatively or additionally, the first arcuate needle passer may be configured such that a portion of the first arcuate needle passer remains within the arcuate channel when the first arcuate tissue puncturing member traverses from the first open end towards the second open end.

Alternatively or additionally, the second arcuate needle passer may be configured such that a portion of the second arcuate needle passer remains within the arcuate channel when the second arcuate tissue puncturing member traverses from the second open end towards the first open end.

Alternatively or additionally, the first region and the second region each include one or more slits formed therein. When the suture shuttle is secured relative to the first arcuate needle passer, the second region is able to flex when the suture shuttle is pushed into the second region by the first arcuate needle passer. When the suture shuttle is secured relative to the second arcuate needle passer, the first region is able to flex when the suture shuttle is pushed into the first region by the second arcuate needle passer.

Alternatively or additionally, the suture device may further include a first latch feature disposed proximate the first open end, the first latch feature configured to releasably secure the suture shuttle at least partially within the first region.

Alternatively or additionally, the suture device may further include a second latch feature disposed proximate the second open end, the second latch feature configured to releasably secure the suture shuttle at least partially within the second region.

In another example, a suture device includes a mounting structure that is connectable to a distal end of an endoscope. A C-shaped suture ring is secured to the mounting structure, the suture ring defining an arcuate channel extending within the suture ring from a first open end to a second open end. A first arcuate needle passer is slidingly disposed within a first side of the arcuate channel, the first arcuate needle pass including a first arcuate tissue puncturing member and a first control end. A second arcuate needle passer is slidingly disposed within a second side of the arcuate channel, the second arcuate needle passer including a second arcuate tissue puncturing member and a second control end. A first control element is operably coupled to the first control end such that translation of the first control element causes the first arcuate needle passer to move within the arcuate channel and a second control element is operably coupled to the second control end such that translation of the second control element causes the second arcuate needle passer to move within the arcuate channel. A suture shuttle is reversibly securable to each of the first arcuate needle passer and the second arcuate needle passer such that the suture shuttle can be passed therebetween.

Alternatively or additionally, the suture shuttle may include a shuttle body defining a straight lumen extending therethrough, the shuttle body configured to fit at least partially within the first region and/or the second region.

Alternatively or additionally, the suture shuttle may be releasably securable to the first arcuate needle passer via an interference fit between the first arcuate tissue puncturing member and the straight lumen.

Alternatively or additionally, the suture shuttle may be releasably securable to the second arcuate needle passer via an interference fit between the second arcuate tissue puncturing member and the straight lumen.

Alternatively or additionally, the first arcuate needle passer may be configured such that a portion of the first arcuate needle passer remains within the arcuate channel when the first arcuate tissue puncturing member traverses from the first open end towards the second open end.

Alternatively or additionally, the second arcuate needle passer may be configured such that a portion of the second arcuate needle passer remains within the arcuate channel when the second arcuate tissue puncturing member traverses from the second open end towards the first open end.

In another example, a suture device includes a mounting structure that is connectable to a distal end of an endoscope. A suture ring is secured to the mounting structure, the suture ring defining an arcuate channel extending within the suture ring from a first open end to a second open end, the suture ring including a first region proximate the first open end and a second region proximate the second open end. A suture shuttle includes a shuttle body defining a straight lumen extending therethrough, the shuttle body configured to fit at least partially within the first region and/or the second region. A first arcuate needle passer is slidingly disposed within a first side of the arcuate channel, the first arcuate needle pass including a first arcuate tissue puncturing member and a first control end, the first arcuate tissue puncturing member releasably forming an interference fit within the straight lumen. A second arcuate needle passer is slidingly disposed within a second side of the arcuate channel, the second arcuate needle passer including a second arcuate tissue puncturing member and a second control end, the second arcuate tissue puncturing member releasably forming an interference fit within the straight lumen.

Alternatively or additionally, the first arcuate needle passer may be configured such that a portion of the first arcuate needle passer remains within the arcuate channel when the first arcuate tissue puncturing member traverses from the first open end towards the second open end.

Alternatively or additionally, the second arcuate needle passer may be configured such that a portion of the second arcuate needle passer remains within the arcuate channel when the second arcuate tissue puncturing member traverses from the second open end towards the first open end.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
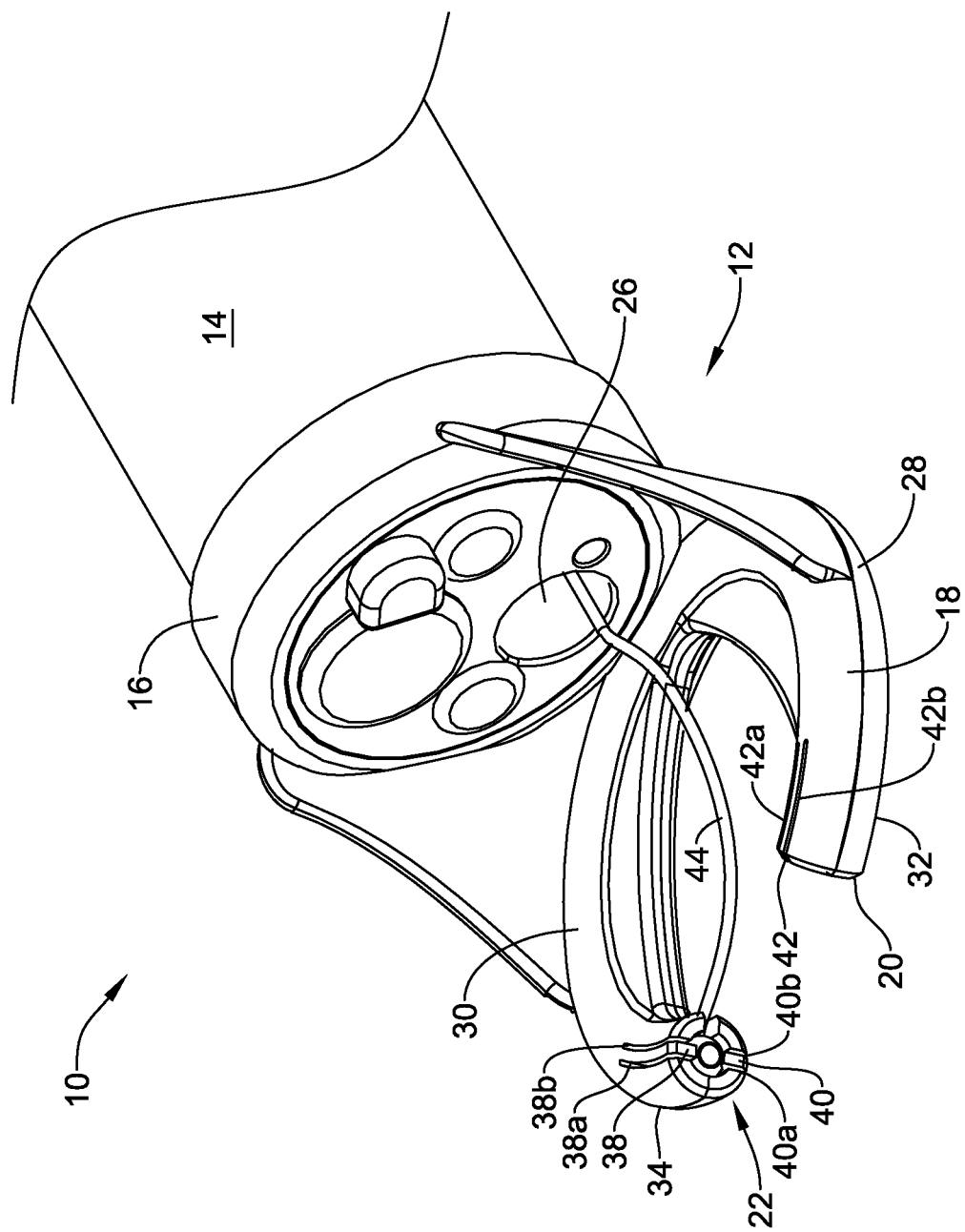
FIG. 1 is a perspective view of an illustrative assembly including an illustrative suture device secured to a distal end of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used in combination with a single working channel endoscope or a dual working channel endoscope within a single working or available channel of an endoscope, and in some cases may be operated by a single individual, although in some cases a second individual may be involved.

FIG. 1 is a perspective view of an illustrative assembly 10 that includes an illustrative suture device 12 secured relative to an endoscope 14. In general, a first device being adapted to be secured relative to a second device includes the first device being secured directly to the second device and also includes the first device being secured to the second device with one or more intervening structures. The suture device 12 may be used in combination with a variety of different endoscopes 14, including but not limited to endoscopes 14 that have a primary working channel with a 2.8 millimeter (mm) diameter, a 3.2 mm diameter or a 3.7 mm diameter. It is also understood that the suture device 10 may be used with any of an endoscope, colonoscope, gastroscope, duodenoscope, bronchoscope, uretoscope, catheter, medical device, or the like. The suture device 12 is easy to use because it only requires one operation by a user at the proximal end in order to make a stitch. No tissue acquisition device like a helix or a grasper is necessary, but one can be used if desired.

As shown, the illustrative suture device 12 includes an end cap ring 16 that is configured to secure the suture device 12 relative to the endoscope 14. For example, the end cap ring 16 may be any over-the-scope connector. In some instances, the suture device 12 may instead include other structures or features (not illustrated) that are adapted to secure the suture device 12 relative to the endoscope 14. The suture device 12 includes a C-shaped suture ring 18. As will be shown with respect to subsequent drawings, the C-shaped suture ring 18 is adapted to permit arcuate-shaped needle passers to slide within the C-shaped suture ring 18 in order to pass a suture shuttle (not visible in FIG. 1) back and forth between a pair of arcuate-shaped needle passers.

The C-shaped suture ring 18 may be considered as tracing out a circle, apart from a missing part of the circle as shown between a first open end 20 and a second open end 22. The missing part of the circle may be considered as defining a region 24 that can accommodate tissue therein to be sutured. In some instances, the relative dimensions of the C-shaped suture ring 18, including the relative distance between the first open end 20 and the second open end 22 may be varied in order to accommodate different tissues, different relative needle passer sizes, and the like. The C-shaped suture ring 18 may be considered as including a first side 28 and a second side 30. The first side 28 of the C-shaped suture ring 18 is to the right (in the illustrated orientation) and the second side 30 of the C-shaped suture ring is to the left.

Additionally, as shown the C-shaped suture ring 18 may be considered as forming a particular arcuate angle relative to the end cap ring 16. This is merely illustrative, as the C-shaped suture ring 18 may be disposed at any desired angle relative to the end cap ring 16. The angle can vary. In some cases, the location of the working region 24 may vary relative to the working channel of the endoscope. The C-shaped suture ring 18 may be attached at any desired position relative to the end cap 16. In some cases, the relative position of the C-shaped suture ring 18 may be adjusted after delivery. In some cases, the suture device 12 may be secured relative to the endoscope 14 such that the region 24 is centered or at least substantially centered relative to a main working channel 26 of the endoscope 14, although this is not required in all cases. While additional tools are not necessary for usage of the suture device 12, in some cases there may be a desire to provide tools through the working channel 26 that can reach the region 24. For example, there may be a desire to use a helix or other grasper to help pull tissue towards the region 24, or to hold tissue relative to the region 24, while suturing. The region 24 may, therefore, also be considered as a working space for the suture device 12.

The suture ring 18 may be considered as having a first region 32 that is disposed proximate the first open end 20 and a second region 34 that is disposed proximate the second open end 22. The first region 32 and the second region 34 each include one or more latching features that are configured to help releasably secure a suture shuttle 36 (better seen in FIG. 2) within either the first region 32 or the second region 34. In the illustrated orientation, it can be seen that the second region 34 includes a first latching feature 38 and a second latching feature 40. It will be appreciated that the first open end 20 includes similar first and second latching features, even though not seen in the illustrated orientation. The first latching feature 38 may be considered as being defined at least in part upon a pair of slits 38a and 38b that extend through the second region 34 from the second open end 22. In some cases, the first latching feature 38 may instead be provided by other latching mechanisms that may include plungers and springs, for example. The second latching feature 40 may be considered as being defined at least in part by a pair of slits 40a and 40b that extend into the second region 34 from the second open end 22. In some cases, the second latching feature 40 may instead be provided by other latching mechanisms that may include plungers and springs, for example. A first latching feature 42 is partially visible at the first open end 20, defined at least in part by a pair of slots 42a and 42b. A suture 44 extends out of the working channel 26 of the endoscope 14, and extends to the suture shuttle 36.

Figure 2:
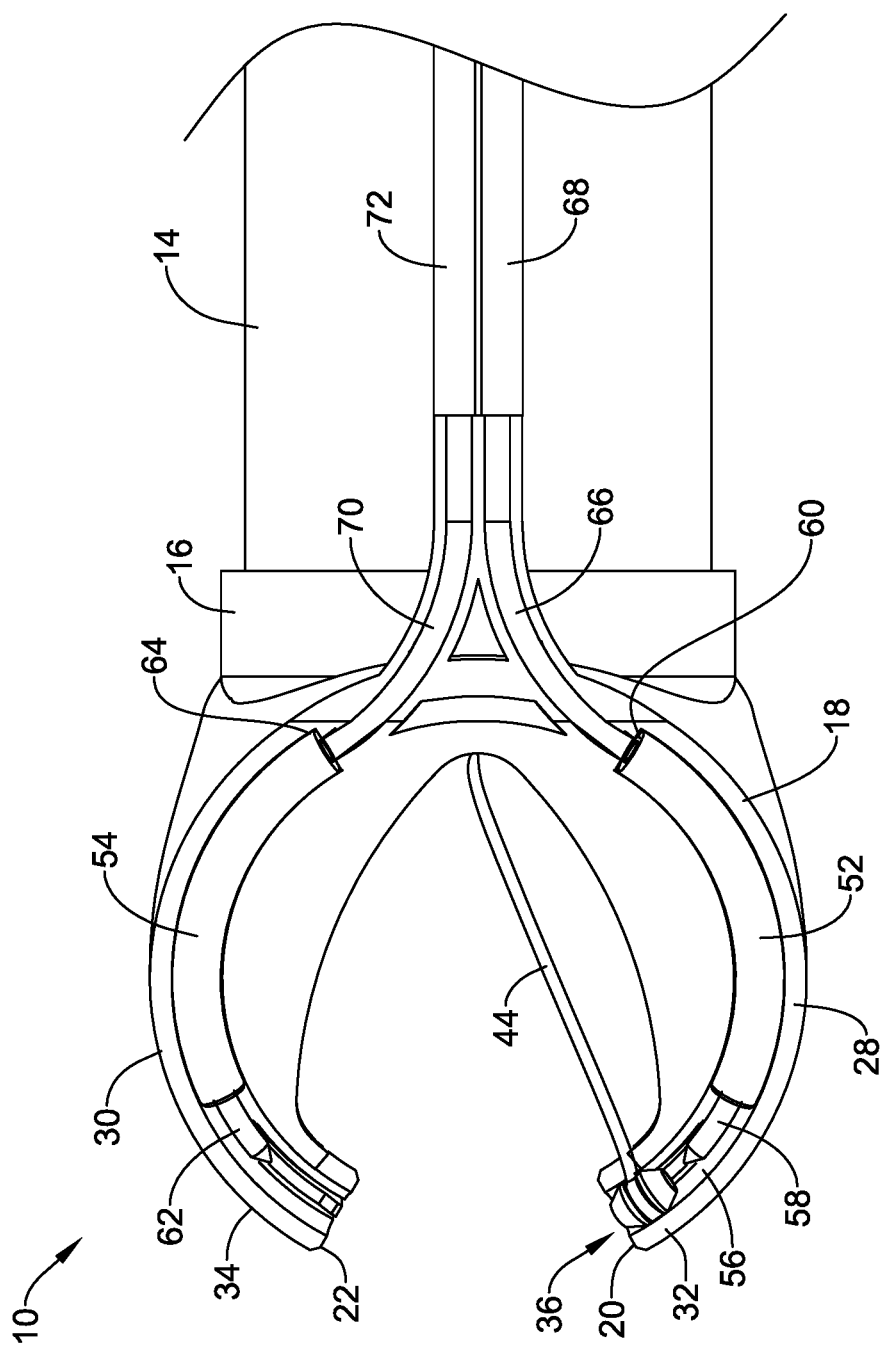
FIG. 2 is a partial cut-away top view of the illustrative suture device of FIG. 1.

FIG. 2 is a partially cut-away top view of the assembly 10 in which a portion of the suture ring 12 has been cutaway to reveal further details of the suture device 12. The suture device 12 includes a first arcuate needle passer 52 disposed within the first side 28 of the suture ring 12 and a second arcuate needle passer 54 that is disposed within the second side 30 of the suture ring 12. As can be seen in FIG. 2, the suture ring 12 defines an arcuate channel 56 within which the first arcuate needle passer 52 and the second arcuate needle passer 54 can move. In some cases, the first arcuate needle passer 52 and the second arcuate needle passer 54 may have an overall diameter that is about the same as an inner diameter of the arcuate channel 56, allowing the first arcuate needle passer 52 and the second arcuate needle passer 54 to move within the arcuate channel 56 while keeping the first arcuate needle passer 52 and the second arcuate needle passer 54 from moving in a direction other than back and forth within the arcuate channel 56.

The first arcuate needle passer 52 includes a first tissue puncturing member 58 and a first control end 60. The second arcuate needle passer 54 includes a second tissue puncturing member 62 and a second control end 64. The first tissue puncturing member 58 and the second tissue puncturing member 62 may be seen as tapering to a point, which facilitates advancing the first arcuate needle passer 52 and the second arcuate needle passer 54 through tissue. A first control element 66 may be seen as being operably coupled with the first control end 60 and extends proximally through a first tubular member 68. A second control element 70 may be seen as being operably coupled with the second control end 64 and extends proximally through a second tubular member 72. The first control element 66 and the second control element 70 may extend proximally to a handle (not shown) and may be individually actuated. In some cases, pulling on the first control element 66 may cause the first arcuate needle passer 52 to pull back farther away from the second open end 20 while pushing on the first control element 66 may cause the first arcuate needle passer 52 to move towards the second open end 22. Pulling on the second control element 70 may cause the second arcuate needle passer 54 to pull back away from the first open end 20 while pushing on the second control element 70 may cause the second arcuate needle passer 54 to move towards the first open end 20. The first control element 66 and the second control element 70 may be individually actuatable, for example. It will be appreciated that in some cases, other actuation mechanisms may be used that include gears or levers, such that the directional force applied at the handle end may be opposite the applied force at the distal end.

The suture shuttle 36 is configured to be moveable back and forth between the first region 32 and the second region 34 by alternately utilizing the first arcuate needle passer 52 to capture and move the suture shuttle 36 from the first region 32, across the working region 24, and to the second region 34, and using the second arcuate needle passer 54 to capture and move the suture shuttle 36 from the second region 34, across the working region 24, and to the first region 32. With tissue pulled into the working region 24, such as by using a grasper, it will be appreciated that the suture 44 can be pulled back and forth through the tissue being sutured.

Figure 3:
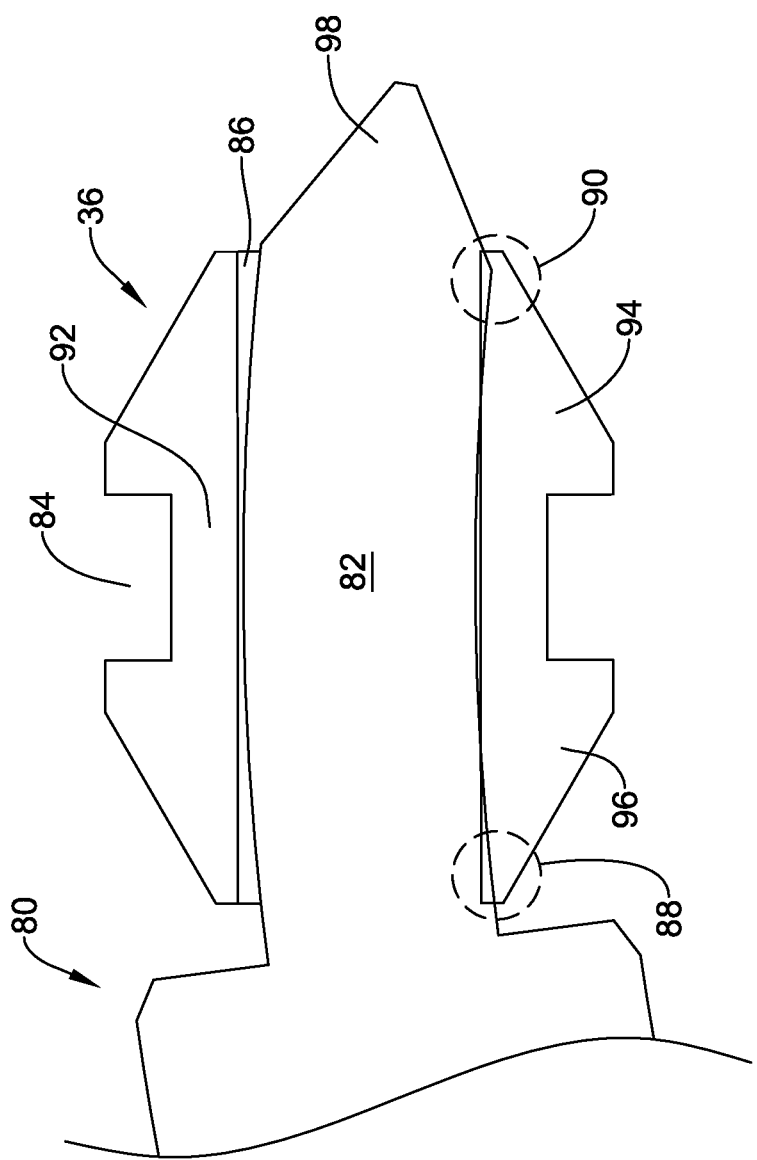
FIG. 3 is a schematic cross-sectional view, showing an interference fit between a needle passer and a suture shuttle, both forming a portion of the illustrative suture device of FIG. 1.

FIG. 3 is a schematic cross-sectional view, showing an interference fit between an arcuate needle passer 80 having an arcuate tissue puncturing member 82 and the suture shuttle 36. The arcuate needle passer 80 may be considered as representing either the first arcuate needle passer 52 or the second arcuate needle passer 54, for example. The suture shuttle 36 includes an annular groove 84 that extends circumferentially about the suture shuttle 36, and is configured to accommodate the suture 44 therein. The suture 44 can be wrapped around the annular groove 84, for example, and then can be knotted to itself to secure the suture 44 relative to the suture shuttle 36. In some cases, the suture 44 may remain secured to the suture shuttle 36, and the suture shuttle 36 may be used in terminating a suture within tissue. In some cases, depending on the particular tissue being sutured, the suture shuttle 36 may be used in combination with a pledget in securing and terminating the suture. The suture shuttle 36 may be considered as being configured to be atraumatic, which may be beneficial when used in terminating a suture within tissue, as this means that the suture shuttle 36 remains within the patient.

The suture shuttle 36 includes a straight lumen 86 that extends through the suture shuttle 36. As seen, the arcuate tissue puncturing member 82, which may be considered as representing the first arcuate tissue puncturing member 58 and/or the second arcuate tissue puncturing member 62 is not straight, but has a curvature to it. As a result, the arcuate tissue puncturing member 82 may be considered as forming an interference fit with the straight lumen 86. Points 88 and 90 illustrate where an interference fit may form, as either the arcuate tissue puncturing member 82 or an inner surface of the straight lumen 86 may have to yield. The interference fit is sufficient to hold the suture shuttle 36 relative to the arcuate tissue puncturing member 82 and thus relative to the arcuate needle passer 80.

The suture shuttle 36 includes a suture shuttle body 92 that includes a first tapered end 94 and a second tapered end 96. In the illustrated orientation, it can be seen that the first tapered end 94 roughly aligns with a terminal end 98 of the arcuate tissue puncturing member 82. If the arcuate needle passer 80 was entering the straight lumen 86 from the opposite direction as illustrated, it will be appreciated that the second tapered end 96 would roughly align with the terminal end 98.

Figure 4:
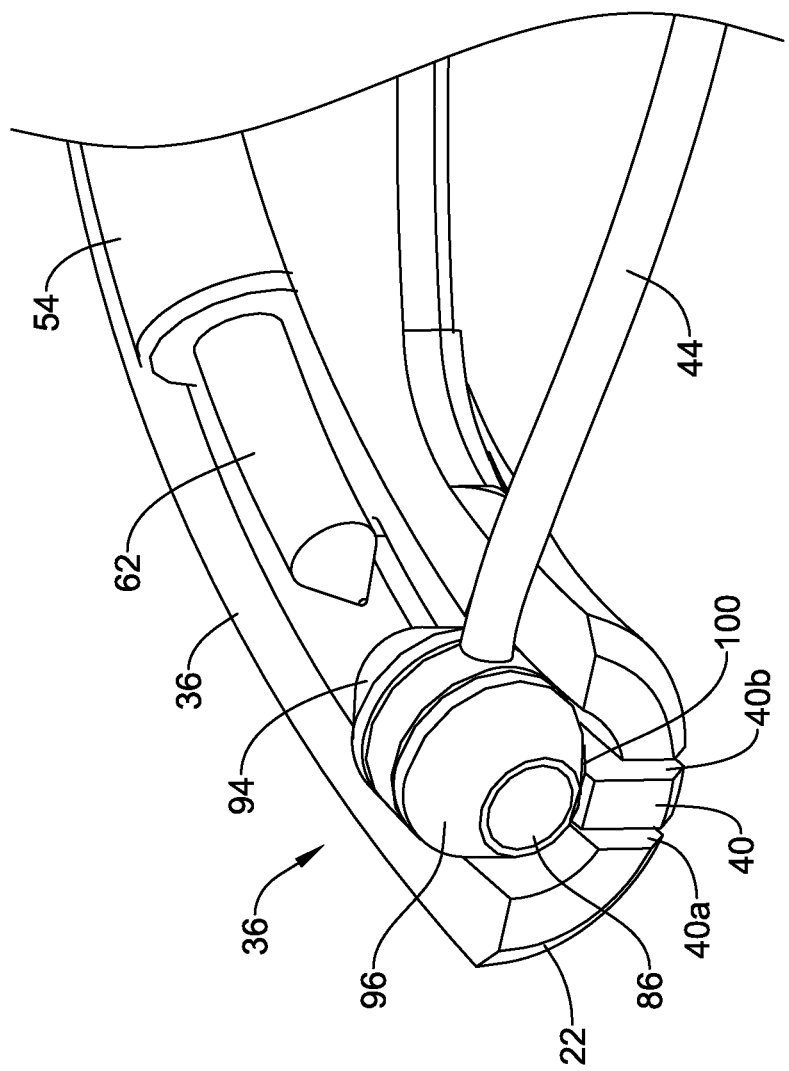
FIG. 4 is a partial cut-away view of the portion of the illustrative suture device of FIG. 1.

FIG. 4 is a partial cut-away view of the a portion of the illustrative suture device 12. In particular, FIG. 4 shows a portion of the second side 30, including the second arcuate needle passer 54. The second latching feature 40, defined at least in part upon the slots 40a and 40b, can be seen as including a ramped surface 100 that engages the second tapered end 96 of the suture shuttle body 92. After the suture shuttle 36 has been pushed into the second region 34, the retention force that is applied to the suture shuttle 36 by the ramped surface 100 exceeds the interference fit between the first tissue puncturing member 58 and the straight lumen 86, and thus the first arcuate needle passer 52 could be withdrawn, leaving the suture shuttle 36 in the location illustrated in FIG. 4. It will be appreciated that each of the latching features, including the latching feature 38 at the second open end 22, the latching feature 42 at the first open end 20 and the latching feature not visible at the first open end 20 would each have a ramped surface such as the ramped surface 100.

Figure 5:
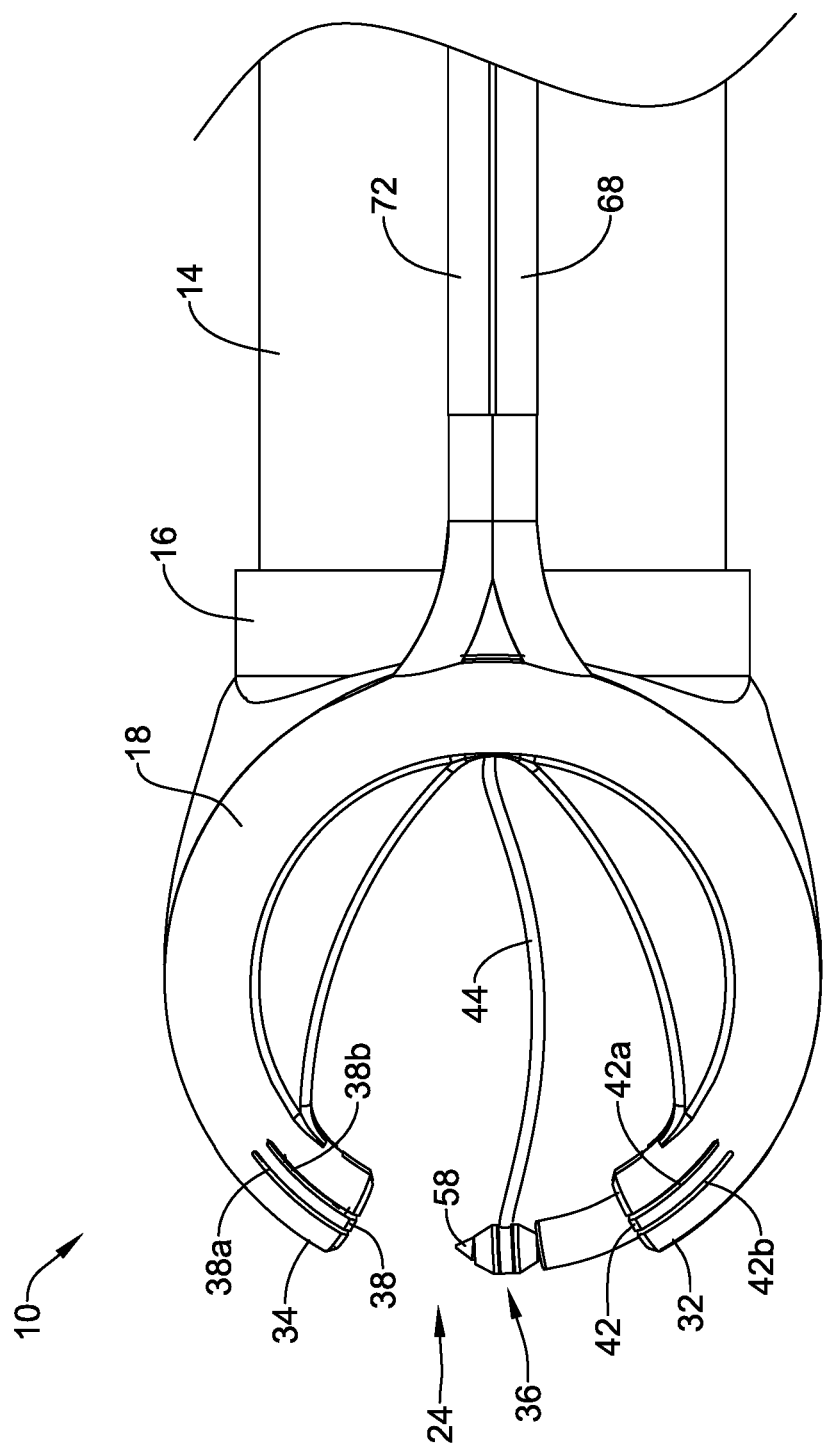
FIGS. 5 through 7 are partial cut-away views of the illustrative suture device of FIG. 1, showing step by step how the suture shuttle is passed from a first arcuate needle passer to a second arcuate needle passer.
Figure 6:
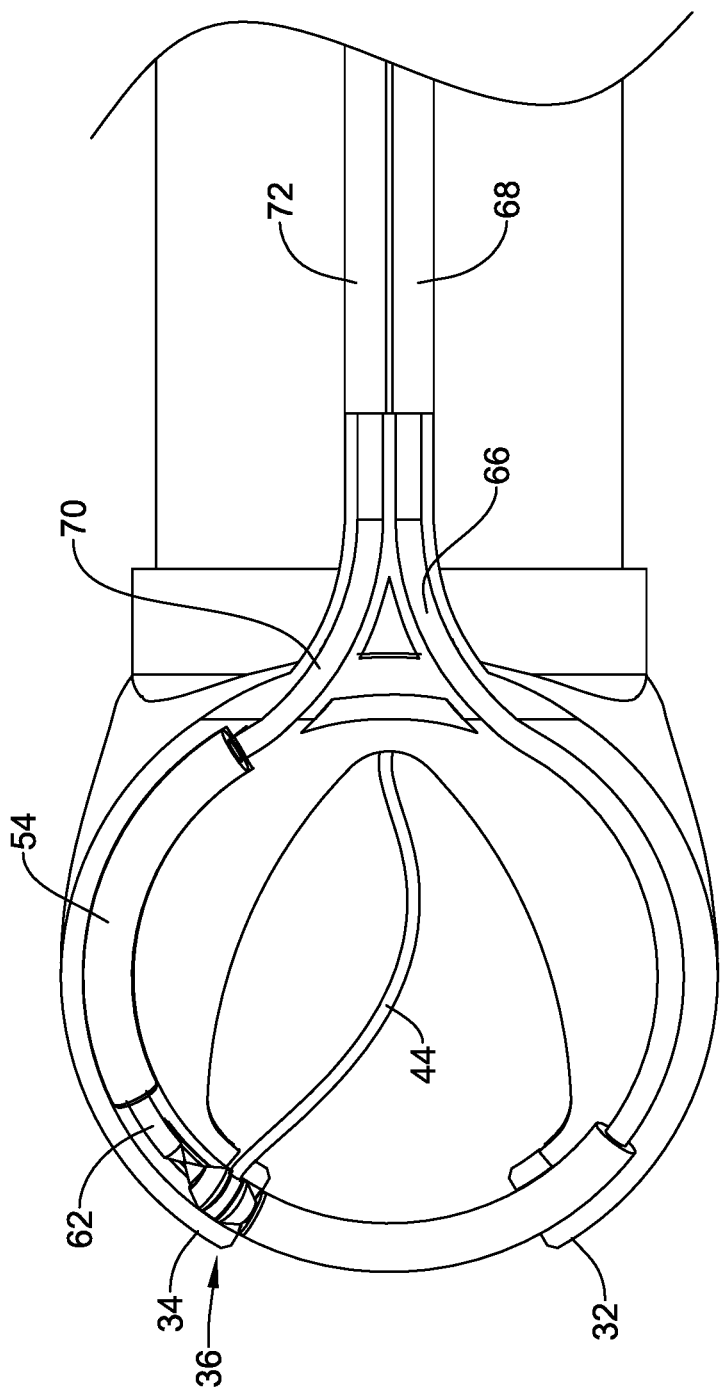
Figure 7:
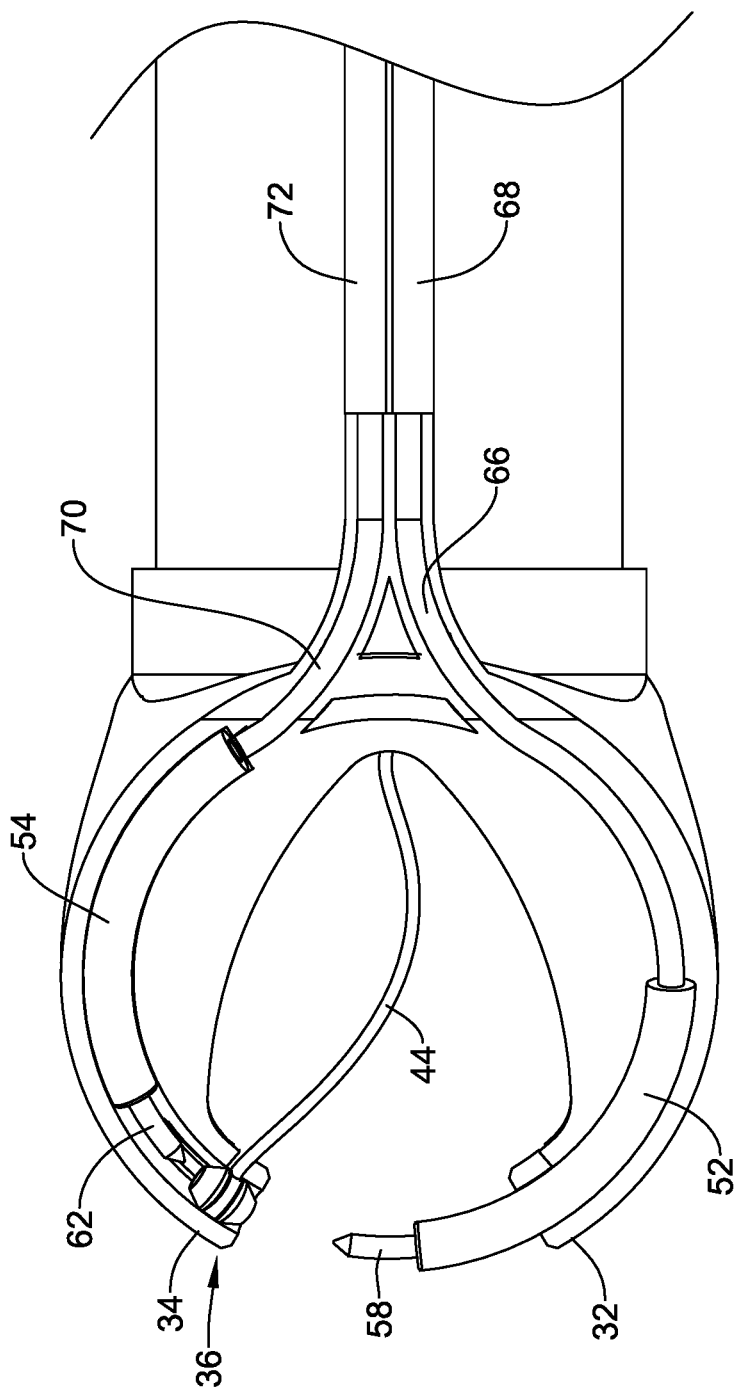

FIGS. 5 through 7 are partial cut-away views of the illustrative suture device 12 FIG. 1, showing step by step how the suture shuttle 36 is passed back and forth. In FIG. 5, the suture shuttle 36 has been pushed by the first control element 66 (not seen in FIG. 5) out into the working region 24. As noted, the arcuate channel 56 has an inner diameter that is a tight fit on an outer diameter of the first arcuate needle passer 52 such that the first arcuate needle passer 52 is held in alignment as the first tissue puncturing member 58 extend through the working region 24, and through any tissue within the working region 24. The suture shuttle 36 may be pushed across the working region 24 and into the second region 22. The latching features 38 and 40 of the second region 34 will engage the suture shuttle 36, as seen in FIG. 6. The first arcuate needle passer 52 may then be withdrawn, leaving the suture shuttle 36 secured within the region 34, as seen in FIG. 7. It will be appreciated that this process can be repeated going in the opposite direction. Once a suture has been placed through the tissue, the suture device 12 can be repositioned in order to place a stitch going in the opposite direction.

It will be appreciated that a variety of different materials may be used in forming the devices described herein. In some cases, a variety of different metals may be used. Illustrative but non-limiting examples of suitable metals include titanium, stainless steel, magnesium, cobalt chromium and others. In some cases, the first control element 46 and the second control element may be made of Nitinol. In some embodiments, for example, the devices described herein may include any suitable polymeric material, including biocompatible materials such as polyurethane or silicone. Suitable polymers include PEEK (polyetheretherketone) and Polycarbonate. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A suture device comprising:
a mount connectable to a distal end of an endoscope;
a suture ring secured to the mount, the suture ring defining an arcuate channel extending within the suture ring from a first open end to a second open end, the suture ring including a first region proximate the first open end and a second region proximate the second open end;
a first arcuate needle passer slidingly disposed within a first side of the arcuate channel, the first arcuate needle passer including a first arcuate tissue puncturing member and a first control end;
a second arcuate needle passer slidingly disposed within a second side of the arcuate channel, the second arcuate needle passer including a second arcuate tissue puncturing member and a second control end; and
a suture shuttle reversibly securable to each of the first arcuate needle passer and the second arcuate needle passer such that the suture shuttle can be passed therebetween.

2. The medical device of claim 1, wherein the suture shuttle includes a shuttle body defining a straight lumen extending therethrough, the shuttle body configured to fit at least partially within the first region and/or the second region.

3. The medical device of claim 2, wherein the suture shuttle is releasably securable to the first arcuate needle passer via an interference fit between the first arcuate tissue puncturing member and the straight lumen.

4. The medical device of claim 2, wherein the suture shuttle is releasably securable to the second arcuate needle passer via an interference fit between the second arcuate tissue puncturing member and the straight lumen.

5. The medical device of claim 1, further comprising:
a first control element operably coupled to the first control end such that translation of the first control element causes the first arcuate needle passer to move within the arcuate channel; and
a second control element operably coupled to the second control end such that translation of the second control element causes the second arcuate needle passer to move within the arcuate channel.

6. The medical device of claim 1, wherein the suture ring extends in a circle from the first open end to the second open end, the first open end and the second open end spaced apart a distance that permits tissue to extend therebetween.

7. The medical device of claim 1, wherein the first arcuate needle passer is configured such that a portion of the first arcuate needle passer remains within the arcuate channel when the first arcuate tissue puncturing member traverses from the first open end towards the second open end.

8. The medical device of claim 1, wherein the second arcuate needle passer is configured such that a portion of the second arcuate needle passer remains within the arcuate channel when the second arcuate tissue puncturing member traverses from the second open end towards the first open end.

9. The medical device of claim 1, wherein the first region and the second region each include one or more slits formed therein;
wherein when the suture shuttle is secured to the first arcuate needle passer, the second region is able to flex when the suture shuttle is pushed into the second region by the first arcuate needle passer; and
wherein when the suture shuttle is secured to the second arcuate needle passer, the first region is able to flex when the suture shuttle is pushed into the first region by the second arcuate needle passer.

10. The medical device of claim 1, further comprising a first latch feature disposed proximate the first open end, the first latch feature configured to releasably secure the suture shuttle at least partially within the first region.

11. The medical device of claim 10, further comprising a second latch feature disposed proximate the second open end, the second latch feature configured to releasably secure the suture shuttle at least partially within the second region.

12. A medical device comprising:
a mount connectable to a distal end of an endoscope;
a C-shaped suture ring secured to the mount, the suture ring defining an arcuate channel extending within the suture ring from a first open end to a second open end;
a first arcuate needle passer slidingly disposed within a first side of the arcuate channel, the first arcuate needle passer including a first arcuate tissue puncturing member and a first control end;
a second arcuate needle passer slidingly disposed within a second side of the arcuate channel, the second arcuate needle passer including a second arcuate tissue puncturing member and a second control end;
a first control element operably coupled to the first control end such that translation of the first control element causes the first arcuate needle passer to move within the arcuate channel;
a second control element operably coupled to the second control end such that translation of the second control element causes the second arcuate needle passer to move within the arcuate channel; and
a suture shuttle reversibly securable to each of the first arcuate needle passer and the second arcuate needle passer such that the suture shuttle can be passed therebetween.

13. The medical device of claim 12, wherein the suture shuttle includes a shuttle body defining a straight lumen extending therethrough, the shuttle body configured to fit at least partially within the first region and/or the second region.

14. The medical device of claim 13, wherein the suture shuttle is releasably securable to the first arcuate needle passer via an interference fit between the first arcuate tissue puncturing member and the straight lumen.

15. The medical device of claim 13, wherein the suture shuttle is releasably securable to the second arcuate needle passer via an interference fit between the second arcuate tissue puncturing member and the straight lumen.

16. The medical device of claim 13, wherein the first arcuate needle passer is configured such that a portion of the first arcuate needle passer remains within the arcuate channel when the first arcuate tissue puncturing member traverses from the first open end towards the second open end.

17. The medical device of claim 13, wherein the second arcuate needle passer is configured such that a portion of the second arcuate needle passer remains within the arcuate channel when the second arcuate tissue puncturing member traverses from the second open end towards the first open end.

18. A medical device comprising:
   a mount connectable to a distal end of an endoscope;
   a suture ring secured to the mount, the suture ring defining an arcuate channel extending within the suture ring from a first open end to a second open end, the suture ring including a first region proximate the first open end and a second region proximate the second open end;
   a suture shuttle including a shuttle body defining a straight lumen extending therethrough, the shuttle body configured to fit at least partially within the first region and/or the second region;
   a first arcuate needle passer slidingly disposed within a first side of the arcuate channel, the first arcuate needle passer including a first arcuate tissue puncturing member and a first control end, the first arcuate tissue puncturing member releasably forming an interference fit within the straight lumen; and
   a second arcuate needle passer slidingly disposed within a second side of the arcuate channel, the second arcuate needle passer including a second arcuate tissue puncturing member and a second control end, the second arcuate tissue puncturing member releasably forming an interference fit within the straight lumen.

19. The medical device of claim 18, wherein the first arcuate needle passer is configured such that a portion of the first arcuate needle passer remains within the arcuate channel when the first arcuate tissue puncturing member traverses from the first open end towards the second open end.

20. The medical device of claim 18, wherein the second arcuate needle passer is configured such that a portion of the second arcuate needle passer remains within the arcuate channel when the second arcuate tissue puncturing member traverses from the second open end towards the first open end.

* * * * *